United States Patent
Koerner

(10) Patent No.: US 10,406,304 B2
(45) Date of Patent: Sep. 10, 2019

(54) DISPENSER HAVING ELECTRONIC ACTUATION DETECTION

(71) Applicant: APTAR RADOLFZELL GMBH, Radolfzell (DE)

(72) Inventor: Joachim Koerner, Uhldingen-Muehlhofen (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 0 days.

(21) Appl. No.: 15/122,464

(22) PCT Filed: Jan. 30, 2015

(86) PCT No.: PCT/EP2015/051985
§ 371 (c)(1),
(2) Date: Aug. 30, 2016

(87) PCT Pub. No.: WO2015/139873
PCT Pub. Date: Sep. 24, 2015

(65) Prior Publication Data
US 2017/0065777 A1 Mar. 9, 2017

(30) Foreign Application Priority Data
Mar. 17, 2014 (DE) ........................ 10 2014 204 939

(51) Int. Cl.
*A61M 15/00* (2006.01)
*B05B 11/00* (2006.01)
(Continued)

(52) U.S. Cl.
CPC ........ *A61M 15/008* (2014.02); *A61M 15/009* (2013.01); *B05B 11/308* (2013.01);
(Continued)

(58) Field of Classification Search
CPC ........................... B05B 11/308; B05B 12/008
See application file for complete search history.

(56) References Cited

U.S. PATENT DOCUMENTS 6,958,691 B1 * 10/2005 Anderson ............ A61B 5/0002
340/539.12
7,849,851 B2 12/2010 Zierenberg et al.
(Continued)

FOREIGN PATENT DOCUMENTS

CA      2 757 195 A1    5/2013
DE  10 2004 009 435 A1  12/2005
(Continued)

OTHER PUBLICATIONS

International Search Report issued in Application No. PCT/EP2015/051985 with English translation, dated Apr. 14, 2015 (7 pages).
(Continued)

*Primary Examiner* — J C Jacyna
(74) *Attorney, Agent, or Firm* — Flynn Thiel, P.C.

(57) ABSTRACT

A dispenser for dispensing a pharmaceutical medium, including a sensor for sensing a dispensing operation and an electronic processing circuit for sensing and further processing a signal caused by the sensor. In order to simplify the design, the sensor is part of a sensor unit, which has a radio transmitter for producing a radio signal, and the processing circuit has a radio receiver designed to receive the radio signal produced by the radio transmitter.

15 Claims, 2 Drawing Sheets

(51) Int. Cl.
*G06F 19/00* (2018.01)
*B05B 12/00* (2018.01)

(52) U.S. Cl.
CPC ........ *B05B 12/004* (2013.01); *G06F 19/3462* (2013.01); *A61M 2205/825* (2013.01); *A61M 2205/8206* (2013.01)

(56) References Cited

U.S. PATENT DOCUMENTS

| | | | |
|---|---|---|---|
| 8,109,414 B2 | 2/2012 | Cater et al. | |
| 8,997,735 B2 | 4/2015 | Zierenberg et al. | |
| 2003/0063524 A1* | 4/2003 | Niemiec | A61B 5/0002 368/10 |
| 2005/0247305 A1 | 11/2005 | Zierenberg et al. | |
| 2007/0163583 A1* | 7/2007 | Brand | A61M 15/0065 128/203.23 |
| 2010/0084433 A1 | 4/2010 | Cater et al. | |
| 2010/0252036 A1* | 10/2010 | Sutherland | A61M 15/00 128/203.12 |
| 2011/0048415 A1 | 3/2011 | Zierenberg et al. | |
| 2012/0080029 A1 | 4/2012 | Koerner et al. | |
| 2013/0119083 A1* | 5/2013 | Ophardt | A47K 5/1204 222/64 |
| 2013/0269685 A1* | 10/2013 | Wachtel | A61M 15/0065 128/200.21 |
| 2014/0039445 A1* | 2/2014 | Austin | G06F 19/3462 604/404 |
| 2014/0131388 A1* | 5/2014 | Heisel | A61M 15/009 222/36 |
| 2014/0144946 A1* | 5/2014 | Kohnle | A61M 15/009 222/36 |
| 2014/0266760 A1* | 9/2014 | Burke, Jr. | G08B 21/24 340/687 |
| 2015/0088057 A1* | 3/2015 | Su | A61M 5/20 604/66 |
| 2015/0352281 A1* | 12/2015 | Pfrang | A61M 15/008 128/203.12 |

FOREIGN PATENT DOCUMENTS

| | | |
|---|---|---|
| DE | 10 2006 050 040 A1 | 4/2008 |
| DE | 10 2008 064 559 A1 | 4/2010 |
| DE | 10 2010 042 007 A1 | 4/2012 |
| EP | 2 439 721 A2 | 4/2012 |
| GB | 2443316 | 4/2008 |
| WO | WO 2014/123858 A1 | 8/2014 |

OTHER PUBLICATIONS

Written Opinion of International Searching Authority issued in Application No. PCT/EP2015/051985 dated Apr. 14, 2015 (6 pages).

* cited by examiner

DISPENSER HAVING ELECTRONIC ACTUATION DETECTION

FIELD OF APPLICATION AND PRIOR ART

The invention relates to a dispenser for dispensing a pharmaceutical medium, comprising a sensor for sensing a dispensing operation and an electronic processing circuit for sensing and further processing a signal caused by the sensor in response to the dispensing operation.

The sensing of dispensing operations in the case of such pharmaceutical dispensers may serve various purposes. In the simplest case, the dispensing operations are sensed in order to be able to count them, so that the patient or a physician can subsequently gain an overview of the dispensing operations that have taken place. However, processing possibilities that go further have also already become known from the prior art, such as for example the sensing of a dispensing operation for the purpose of controlling a blocking mechanism, which is intended to prevent overdosing of the medium. DE 10 2010 042 007 A1 and DE 10 2008 064 559 A1 are cited in connection with the invention as technological background.

Although the technique for sensing a dispensing operation, for example in the form of a simple probe, and the electronic further processing of this dispensing operation require comparatively simple means, among the difficulties that are presented by the development of such dispensers is the difficulty that the location of the sensing of the dispensing operation does not coincide with an appropriate location for arranging the further processing circuit. Thus, for example, in the case of a so-called Metered Dose Inhaler (MDI), a particularly appropriate location for sensing the dispensing operation is provided at a lower end of the housing, where the medium emerging from an integrated container with an outlet stub is diverted in the direction of a dispensing opening of the dispenser, while a processing circuit, including a display in the form of an LC display, is arranged with preference on a lateral body of the dispenser.

It sometimes involves a high degree of structural complexity to galvanically connect the sensor that is arranged in an optimized manner with a view to satisfactory sensing of the dispensing operations to the processing circuit that is arranged with a view to convenient handling. Laying corresponding lines in the dispenser is usually not possible within a fully automated assembly process. Other techniques, such as the printing of conductor tracks onto parts of the plastic housing of a dispenser of the generic type, are usually likewise not commercially expedient.

Then there is also the fact that solutions for such a galvanic connection of the sensor to the processing circuit are usually not interchangeable between dispenser types. Consequently, newly developed dispensers often also have a need for a new concept with regard to the laying of the signal transmission lines.

PROBLEM AND SOLUTION

The problem addressed by the invention is therefore that of further developing a dispenser of the generic type to the extent that it allows the signal transmission between the sensor and the processing circuit in a simple way, it being desired that the individual modifications to dispensers of different types with regard to the sensor, the further processing circuit and their connection are as minor as possible.

This is achieved according to the invention by the sensor being part of a sensor unit, which has a radio transmitter for producing a radio signal. Furthermore, it is provided according to the invention that the processing circuit has a radio receiver, which is designed for receiving the radio signal produced by the radio transmitter.

In the case of a dispenser according to the invention, consequently two electronic subassemblies are provided, which in spite of their integration in a common dispenser are not galvanically coupled to one another. Instead, the interface that connects the electronic subassemblies, on the one hand the sensor unit and on the other hand the processing circuit, to one another is a radio interface. This allows the ideal arrangement for sensing the dispensing operation and for processing, and in particular displaying, the processed signals in each case to be chosen without taking consequent structural problems into consideration. Among the consequent problems mentioned that are avoided by the invention are the structurally complex arrangement of the lines that were previously usually required and the sealing of walls that are passed through by these lines. Especially the possibility of insulating subchambers of the dispenser, for example the one that contains the evaluation module, in a watertight manner is a major advantage of the invention.

The configuration according to the invention can be used in the case of many different types of dispensers, such as for example the "Metered Dose Inhalers" mentioned at the beginning, in the case of which it is provided type-specifically that a container that can be actuated by squeezing and has an outlet stub is inserted into a receiving shaft and is displaced by pressing down the main container body thereof with respect to the outlet stub, and can thereby be actuated. However, other dispenser types, such as for example nasal dispensers and ophthalmic dispensers, can also be improved in an advantageous way by the measures according to the invention. Such dispensers usually have a piston pump, which is manually actuated for the purpose of dispensing liquid. Medical syringes and the special form of such syringes as auto-injectors, may also be developed according to the invention.

The specific configuration of the processing circuit depends on the respectively intended application. The processing circuit comprises at least an energy source in the form of a battery or a rechargeable battery and the radio receiver mentioned. The configuration according to the invention is appropriate in particular for such processing circuits that additionally have a display device, for example an LC display, since the arrangement at a specific position of the dispenser is desired in particular in the case of such processing circuits. As an alternative or in addition to the display device, the processing circuit may however also have a memory, in order to store the dispensing operations, if appropriate while taking the time of the dispensing operation into consideration. Configurations in which the processing circuit has a further radio module, which is capable of passing on data to processing devices remote from the dispenser, are also possible. Such requirements arise for example in the context of so-called telemedicine.

As far as the sensor unit is concerned, at least the sensor and the radio transmitter are provided. In this case, the sensor may be configured in a variety of ways, common to which is that they convert a mechanical variable, in particular a relative displacement of components, or a force or a pressure into a signal that can be electronically evaluated. The simplest form of such a sensor is a probe, which is activated in the course of the actuation of the dispenser. Apart from the variables mentioned, the sensor may however also be intended for the evaluation of other physical variables that undergo a change in the course of a dispensing operation. These also include in particular sensors that sense the mass flow/volumetric flow of the medium.

In principle, in a way similar to the processing circuit, the sensor unit may have an energy source in the form of a battery or a rechargeable battery, which makes available the required energy for the operation of the radio transmitter.

One particular advantage is obtained however if the sensor unit is assigned a conversion device for the conversion of mechanical energy into electrical energy, this conversion device preferably being identical to the sensor. In the case of such a configuration, consequently, the energy that is introduced directly by the user into the system in the course of the dispensing operation is used to convert it at least partially into electrical energy, which can subsequently supply the radio transmitter. Such a conversion device preferably takes the form of the sensor itself. When the conversion device therefore makes electrical energy available, this happens in response to a dispensing operation that is taking place. The sensor unit may accordingly be designed such that it directly emits the radio signal in the presence of this electrical energy.

A piezoelectric conversion device, in particular in the form of a so-called piezo stack, which operates as a piezo generator, comes into consideration in particular as the conversion device. Doing without a battery or a rechargeable battery for the sensor unit is advantageous in particular on account of the easier disposability of the dispenser after use.

In order in spite of the power source being absolutely necessary for the processing circuit to ensure easy disposability, the processing circuit may be provided as a unit on the dispenser that can be detached by the final consumer, which is detached from the dispenser before disposal of the other parts thereof and is passed on for separate disposal or reuse.

The processing circuit and the sensor unit are fixedly connected as intended to subcomponents of the dispenser and are preferably also arranged fixed in place in relation to one another. In order to manage with a particularly low transmitting power of the sensor unit, and in particular to be able to use for the signal transmission a very simple radio pulse that is not amplitude- or frequency-modulated, it is of advantage if the radio transmitter and the radio receiver are arranged no more than 10 cm away from one another on the dispenser. The preferred frequency range in which the radio transmitter and the radio receiver operate lies between 100 kHz and 3 GHz.

The following arrangement is particularly advantageous, in particular in the case of MDIs. The dispenser has a wall which defines therein a receiving region, in which the container is arranged. This receiving region is surrounded by the wall. The sensor mentioned is located within the receiving region, which is understood as meaning that it is arranged aligned within it with respect to the direction of extent of the region. The processing circuit is arranged outside the receiving region with respect to the projection of the region, and is preferably fastened on the outer side of the wall of the receiving region. This is a design that is customary for MDIs, with which the arrangement of the lines has presented difficulties in the past. The proposed radio link is therefore advantageous especially in the case of such an arrangement.

In particular in the case of the configuration mentioned of the sensor unit with a conversion device that supplies the radio transmitter with electrical energy, it is of advantage to accomplish the signal transmission by means of such a simple radio pulse. A simple oscillating circuit, purely by way of example with a resonant frequency of for example 1 GHz, may be used for example for this. If the transmission of more than just one pulse is desired, it is of advantage if recourse is made to a standardized radio transmission method, in particular on the basis of the Bluetooth standard, on the basis of the Zigbee standard, on the basis of the Ant Plus standard, on the basis of the Wibree standard or on the basis of the IEEE 802.15.4 standard. These standards are respectively designed for transmitters and receivers to manage with a small amount of electrical energy. The use of such standards allows a bidirectional communication between the sensor unit and the processing circuit, which can increase the range of applications of dispensers according to the invention.

BRIEF DESCRIPTION OF THE DRAWINGS

Further aspects and advantages emerge from the claims and the following description of two exemplary embodiments of the invention, which are explained with reference to the figures, in which:

DETAILED DESCRIPTION OF THE EXEMPLARY EMBODIMENTS

Figure 1:
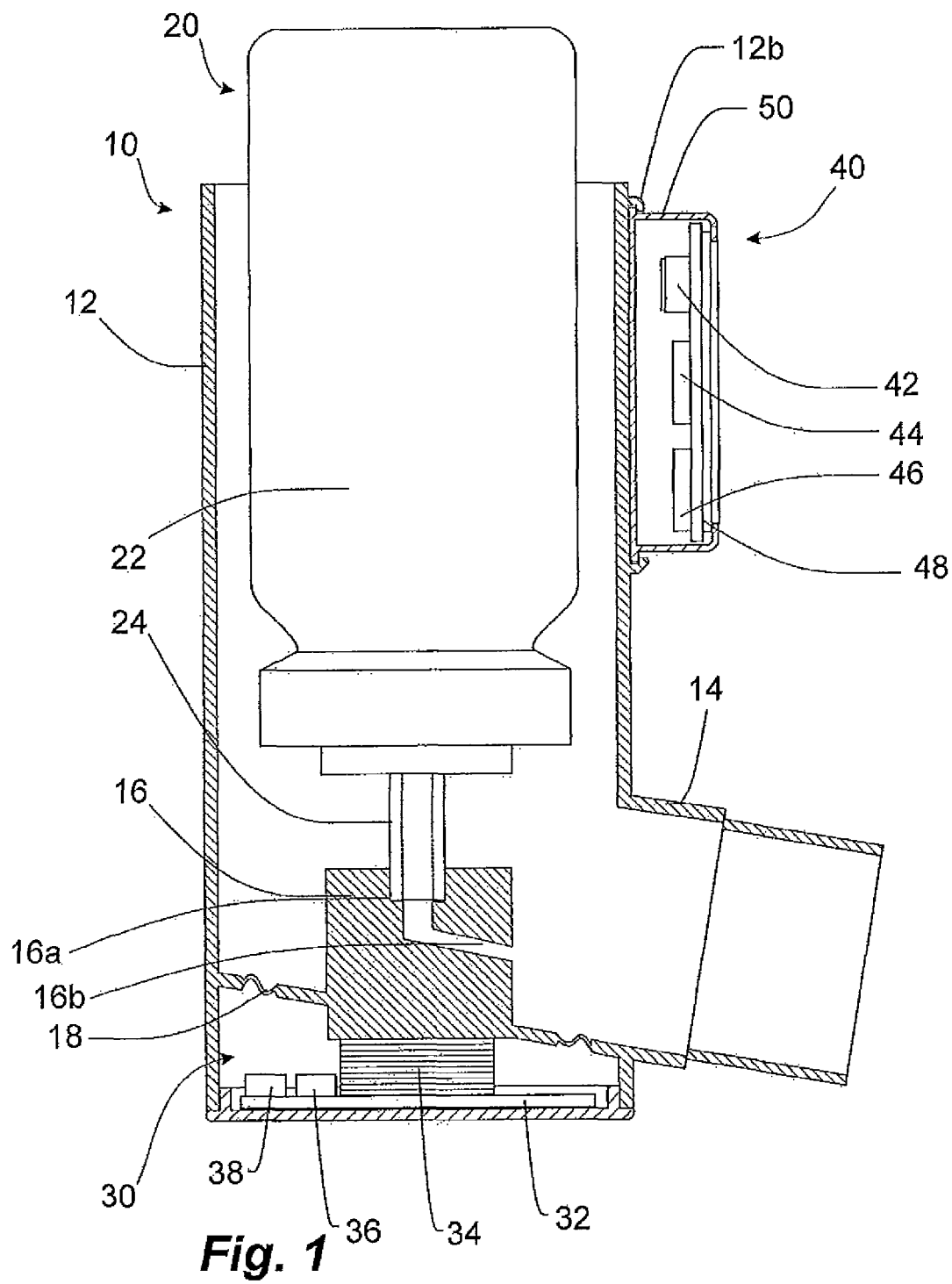
FIG. 1 shows a first embodiment of a dispenser according to the invention.

FIG. 1 shows a first embodiment of a dispenser according to the invention. This is configured in the manner of an MDI (Metered Dose Inhaler). It has a plastic housing 10, which has an approximately cylindrical receiving region defined by a housing wall 12, and also a mouthpiece 14 angled with respect thereto. The receiving region is designed for receiving a container 20. This container 20 has in turn a liquid reservoir 22 and an outlet stub 24, which are displaceable with respect to one another. In this case, the container is designed in such a way that, by pressing down the liquid reservoir 22, a relative displacement with respect to the outlet stub 24 takes place, by which a defined amount of the medium previously stored in the liquid reservoir 22 is dispensed through the outlet stub 24. The outlet stub 24 is accommodated in a receptacle 16a, which belongs to the housing 10 and is adjoined by a dispensing channel 16b. The receptacle 16a and the dispensing channel 16b are provided in a restrictedly displaceable housing portion 16, which is connected to surrounding parts of the housing 10 by means of a thin-walled attachment structure 18. The housing portion 16 is therefore restrictedly movable with respect to the wall 12 and the cylindrical region via the thin-walled attachment structure 18 and the mouthpiece 14 of the dispenser.

For sensing dispensing operations, the dispenser has a sensor unit 30, which is joined onto the housing 10 below the movable housing portion 16. This sensor unit 30 comprises a printed circuit board 32, mounted on which is a piezo stack 34, which is arranged directly underneath the housing portion 16. Connected to the piezo stack 34 is an intermediate energy store 36, for example in the manner of a capacitor. This in turn is coupled to a simple radio transmitter 38 in the manner of a 1 GHz oscillating circuit.

Provided on the outer lateral surface of the wall 12 which defines the cylindrical receiving region of the housing 10 is a processing circuit 40, which has an energy source 42 in the form of a button cell, a processing circuit 44 and a radio receiver 46. Additionally provided is an LC display 48, which is connected to the circuit 44. The processing circuit 40 is inserted in a housing 50, which has been pushed into a mounting 12b on the outer side of the wall 12 which defines the cylindrical receiving region.

When the dispenser is actuated by pressing down the liquid reservoir 22, there is a displacement of the outlet stub 24 with respect to the liquid reservoir 22 and also a displacement of the housing portion 16 with simultaneous compression of the piezo stack 34. The compression of the piezo stack 34 has the effect of generating electrical energy, which is stored in the capacitor 36. The container 20 and the sensor unit 30 are made to match one another in such a way that the energy generated by the piezo stack 34 in the capacitor 36 reaches an energy level that is sufficient for the operation of the radio transmitter 38 shortly before the displacement of the liquid reservoir 22 with respect to the outlet stub 24 is sufficient to bring about the dispensing operation. Consequently, the emission of a radio pulse by the radio transmitter 38 occurs shortly before the dispensing operation.

This radio pulse is received by the radio receiver 46 and passed on to the circuit 44. The latter adds to the number of previous dispensing operations stored in it the one that has just been registered and indicates the result on the LC display 48 for a short time period of several seconds or minutes.

The design of the system with a radio transmitter 38 and a radio receiver 46 achieves the effect that an optimum arrangement both of the sensor 34 and of the display 48 is possible without the problems involved in the arrangement of lines that usually arise in this case having to be taken into consideration.

Figure 2:
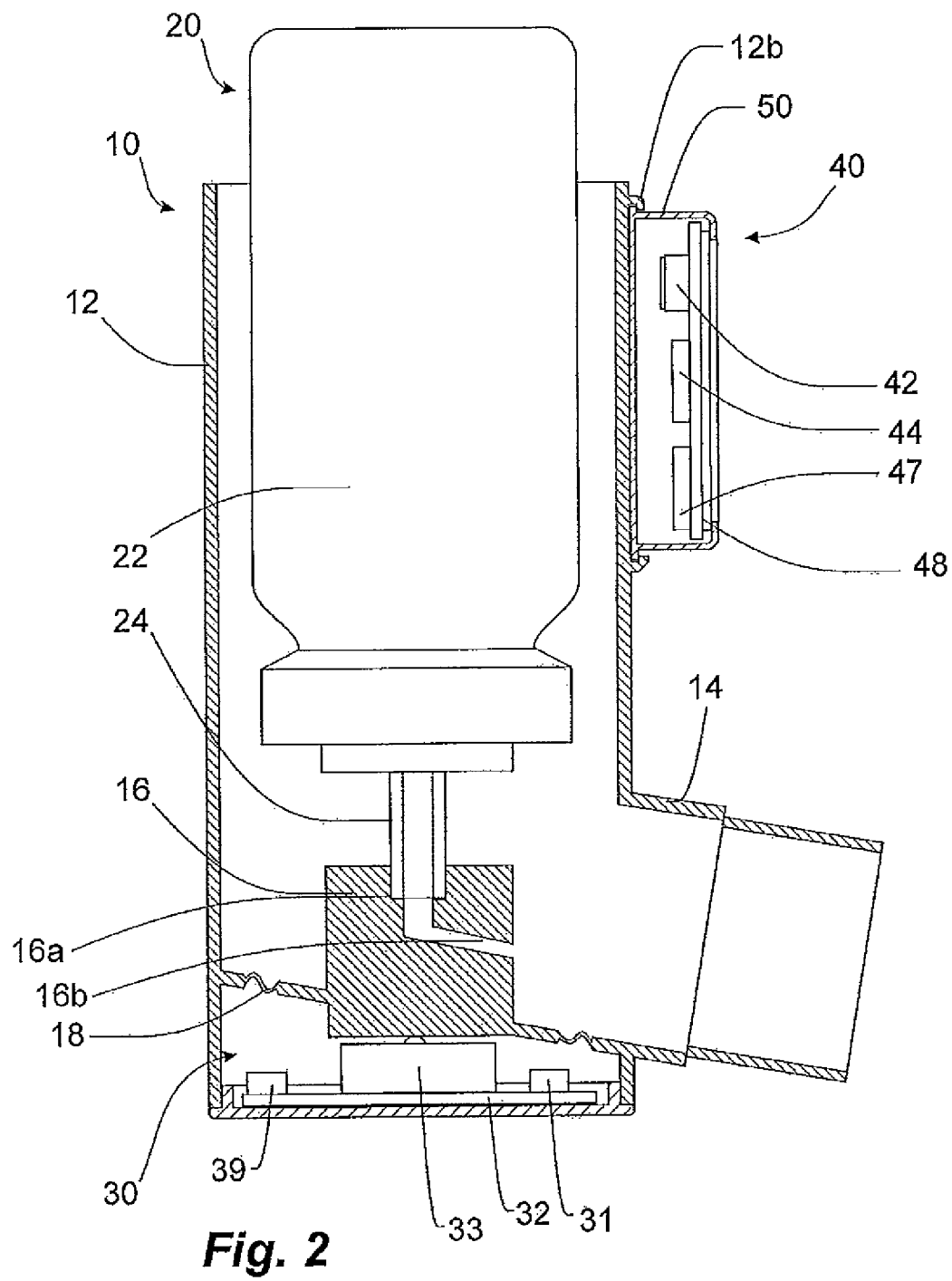
FIG. 2 shows a second embodiment of a dispenser according to the invention.

The embodiment of FIG. 2 is identical to that of FIG. 1 with regard to most aspects. The main difference is that in the case of this second embodiment the sensor unit 30 also has an energy source 31 in the form of a battery and that a simple probe 33 is provided instead of the piezo stack. Furthermore, the radio transmitter 39 and the radio receiver 47 in the case of this second exemplary embodiment are designed as bidirectionally communicating Bluetooth radio units.

The electrical energy for operating the radio device 39 on the sensor unit consequently does not have to be made available by the dispensing operation, and the mechanical energy thereby introduced into the system made available in a converted form, but instead the electrical energy comes directly from the battery 31.

The invention claimed is:

1. A dispenser for dispensing a pharmaceutical medium, comprising:
   a housing defining first and second spaced-apart and separate locations;
   a sensor unit disposed at said first location for sensing a dispensing operation, said sensor unit including a radio transmitter for producing a radio signal, and a conversion device configured to convert mechanical energy generated during a dispensing operation of said dispenser into electrical energy, said sensor unit being configured to supply electrical energy generated by said conversion device to said radio transmitter to operate same to produce the radio signal; and
   an electronic processing circuit disposed at said second location and including a radio receiver configured for receiving the radio signal produced by said radio transmitter;
   said housing including a housing part configured for mounting said electronic processing circuit on said housing, said electronic processing circuit being detachable from said housing part to allow re-use or disposal of said electronic processing circuit.

2. The dispenser of claim 1, wherein said first and second locations are disposed not more than 10 centimeters from one another on said housing.

3. The dispenser of claim 1, wherein said housing includes a housing wall defining therein a receiving region and said dispenser comprises a container disposed in said receiving region, said conversion device being disposed within said receiving region and said electronic processing circuit being disposed outside said receiving region.

4. The dispenser of claim 1, wherein said radio transmitter is configured to produce a radio signal according to the Bluetooth standard, the Wibree standard, the ANT+ standard or the Zigbee standard.

5. The dispenser of claim 1, wherein said electronic processing circuit is configured for counting dispensing operations of said dispenser.

6. The dispenser of claim 1, wherein said housing defines therein a receiving region and said dispenser includes a container disposed in said receiving region, and said conversion device is configured to convert mechanical energy generated during movement of said container within said housing into electrical energy.

7. The dispenser of claim 1, wherein said housing includes a housing wall defining an interior configured for receiving therein a container including therein fluid to be dispensed from said dispenser, said sensor unit being disposed within said interior and said electronic processing circuit being disposed exteriorly of said housing wall and spaced from said sensor unit.

8. A dispenser for dispensing a pharmaceutical medium, said dispenser comprising:
   a housing including a housing wall defining an interior region, said housing defining first and second spaced-apart locations therealong, said first location being located within said interior region and said second location being located exteriorly of said housing wall outside of said interior region;
   a sensor unit disposed at said first location of said housing for sensing a dispensing operation of said dispenser, said sensor unit including a radio transmitter and a conversion device configured to convert mechanical energy generated during a dispensing operation of said dispenser into electrical energy, said conversion device being electrically connected to said radio transmitter for supplying electrical energy thereto to permit said radio transmitter to produce a radio signal;
   a processing unit disposed at said second location of said housing, said processing unit including an electronic processing circuit and a radio receiver configured for receiving a radio signal from said radio transmitter; and
   a container of pharmaceutical medium disposed within said interior region, said conversion device being configured to convert mechanical energy generated during movement of said container relative to said housing into electrical energy;
   said conversion device comprising a piezo stack, said container compressing said piezo stack during movement of said container relative to said housing during a dispensing operation of said dispenser.

9. The dispenser of claim 8, wherein said radio transmitter and said radio receiver are disposed not more than 10 centimeters from one another.

10. The dispenser of claim 8, wherein said sensor unit comprises an intermediate energy storage device electrically connected to said piezo stack and to said radio transmitter such that said intermediate energy storage device supplies electrical energy generated by said piezo stack to said radio transmitter to operate same.

11. The dispenser of claim 10, wherein said intermediate energy storage device comprises a capacitor.

12. The dispenser of claim 1, wherein said housing includes a housing wall defining an interior and said dispenser includes a container disposed in said interior, said housing further including a housing portion movably mounted within said interior of said housing and disposed vertically beneath said container, said container being disposed to permit a downward pressure to be applied to said container by a user to cause discharge of a fluid in said container from said dispenser, wherein a downward pressure applied to said container causes displacement of said housing portion, said sensor unit being disposed within said interior of said housing vertically beneath said housing portion such that displacement of said housing portion causes said conversion device to convert mechanical energy into electrical energy.

13. The dispenser of claim 8, wherein said housing further includes a housing portion movably mounted within said interior region vertically beneath said container, said container being disposed to permit a downward pressure to be applied to said container by a user to cause discharge of pharmaceutical medium in said container from said dispenser, wherein a downward pressure applied to said container causes displacement of said housing portion, said sensor unit being disposed within said interior region of said housing vertically beneath said housing portion such that displacement of said housing portion causes said conversion device to convert mechanical energy into electrical energy.

14. A dispenser for dispensing a pharmaceutical medium, comprising:
  a container of pharmaceutical medium;
  a housing configured to accommodate said container, said container being disposed relative to said housing to permit a downward pressure to be applied to said container by a user to cause a dispensing operation of said dispenser, said housing having first and second spaced-apart locations and including a housing portion, said housing portion being movably mounted within said housing and disposed vertically beneath said container such that a downward pressure applied to said container causes displacement of said housing portion;
  a sensor unit disposed at said first location of said housing for sensing a dispensing operation of said dispenser, said sensor unit including a radio transmitter and a conversion device configured to convert mechanical energy into electrical energy, said conversion device being electrically connected to said radio transmitter for supplying electrical energy thereto to permit said radio transmitter to produce a radio signal, said conversion device being disposed vertically beneath said housing portion such that displacement of said housing portion during a dispensing operation causes said conversion device to convert mechanical energy into electrical energy, said sensor unit in its entirety, including said radio transmitter and said conversion device, being disposed vertically beneath said housing portion; and
  a processing unit disposed on said housing at said second location thereof, said processing unit including an electronic processing circuit and a radio receiver configured for receiving a radio signal from said radio transmitter.

15. A dispenser for dispensing a pharmaceutical medium, comprising:
  a container of pharmaceutical medium;
  a housing configured to accommodate said container, said container being disposed relative to said housing to permit a downward pressure to be applied to said container by a user to cause a dispensing operation of said dispenser, said housing having first and second spaced-apart locations and including a housing portion, said housing portion being movably mounted within said housing and disposed vertically beneath said container such that a downward pressure applied to said container causes displacement of said housing portion;
  a sensor unit disposed at said first location of said housing for sensing a dispensing operation of said dispenser, said sensor unit including a radio transmitter and a conversion device configured to convert mechanical energy into electrical energy, said conversion device being electrically connected to said radio transmitter for supplying electrical energy thereto to permit said radio transmitter to produce a radio signal, said conversion device being disposed vertically beneath said housing portion such that displacement of said housing portion during a dispensing operation causes said conversion device to convert mechanical energy into electrical energy; and
  a processing unit disposed on said housing at said second location thereof, said processing unit including an electronic processing circuit and a radio receiver configured for receiving a radio signal from said radio transmitter;
  said housing including a housing wall defining an interior in which said container is disposed, said sensor unit being disposed within said interior vertically beneath said housing portion.

* * * * *